(12) United States Patent
Brugnoli

(10) Patent No.: US 7,621,271 B2
(45) Date of Patent: Nov. 24, 2009

(54) DEVICE FOR THE MEASUREMENT OF OXYGEN CONSUMPTION

(75) Inventor: Paolo Brugnoli, Rome (IT)

(73) Assignee: Cosmed Engineering S.R.I., Pavona di Albano (IT)

( * ) Notice: Subject to any disclaimer, the term of this patent is extended or adjusted under 35 U.S.C. 154(b) by 715 days.

(21) Appl. No.: 11/172,305

(22) Filed: Jun. 30, 2005

(65) Prior Publication Data

US 2006/0005836 A1 Jan. 12, 2006

(30) Foreign Application Priority Data

Jun. 30, 2004 (IT) .......................... RM2004A0323

(51) Int. Cl.
*A61M 11/00* (2006.01)
(52) U.S. Cl. .............................. 128/205.11; 128/204.23
(58) Field of Classification Search ............ 128/205.11, 128/205.12, 204.22, 204.23, 203.22, 203.25, 128/204.18; 600/531
See application file for complete search history.

(56) References Cited

U.S. PATENT DOCUMENTS

| 4,631,966 A | 12/1986 | Brugnoli | |
|---|---|---|---|
| 4,658,832 A | 4/1987 | Brugnoli | |
| 6,475,158 B1 * | 11/2002 | Orr et al. | 600/531 |
| 2006/0241507 A1 * | 10/2006 | Carlson et al. | 600/532 |

* cited by examiner

*Primary Examiner*—Steven O Douglas
(74) *Attorney, Agent, or Firm*—Nixon Peabody LLP

(57) ABSTRACT

Device for the measurement of oxygen consumption which, by use of a mixing chamber of small dimensions, allows compensation of the time delay between the measurement of the ventilation $V_E$ and that of average oxygen concentration of the exhaled air volume $FeO_2$. The time delay between measurement of $V_E$ and $FeO_2$ maintains a constant value under all ventilations, thanks to a dynamic control of the air quantity collected and introduced in the microchamber and to a dynamic update of proportion factor K, performed by a control system. This enables a precise measurement of oxygen consumption also with rapid ventilation changes.

6 Claims, 2 Drawing Sheets

DEVICE FOR THE MEASUREMENT OF OXYGEN CONSUMPTION

FIELD OF THE INVENTION

The present invention relates to a device designed for the measurement of oxygen consumption in clinical, sports medicine and fitness applications.

STATE OF THE ART

Several methods for measuring metabolic rate of human beings during rest or physical activities are known. They are substantially based upon the principle that metabolic processes are associated to production of heat. Some use the method of the so called direct calorimetry, other ones the indirect calorimetry.

In the devices that measure by means of direct calorimetry, the measurement of the heat generated by the body is performed through a "calorimeter" where a patient is kept for the entire duration of a test. The quantity of heat produced is measured with different techniques which depend on the calorimeter used. However. dimensions, cost and technical problems make the use of traditional calorimeter almost impossible for routinely applications such as weight management and fitness.

The devices using the "Indirect Calorimetry" technique, are based on the principle that every liter of oxygen consumed during human breathing corresponds to about 5 Kcal of energy produced. The measure of oxygen consumption $VO_2$ allows to evaluate the energy expenditure EE with the following simple equation:

$$EE(Kcal/\text{day}) = K \cdot VO_2 \text{ (ml/min)}$$

The calculation of oxygen consumption can be represented by way of example by means of the following equation:

$$VO_2 = VE \cdot \frac{(20.93 - FeO2)}{100}$$

Wherein:
$V_E$ expiration ventilation (L/min)
$FeO_2$ mixed expired $O_2$ concentration (%)

$V_E$ represents the quantity of air ventilated by the subject in a minute and it is usually measured by means of a Flowmeter held to mouth. Different flowmeters technologies are available which guarantee a good accuracy and reproducibility of results both at rest or during exercise. The most common types of flowmeters are: turbine, hot wire, pressure difference (pneumotachograph), venturi effect.

$FeO_2$ represents the mixed $O_2$ average concentration in the air expired in a minute, while the value 20.93% is the oxygen concentration in inspired air. There is a difference between the oxygen concentration average in time and average concentration of a gas volume $FeO_2$. To obtain $FeO_2$ it is necessary to perform a mixing of the whole expired volume or to make a complex integration of the flow and concentration signals at mouth, according to the method, "breath by breath".

The measurement of $FeO_2$ can be substantially obtained with the following techniques: Douglas Bags, Mixing Chamber or Breath by Breath. With the first technique (Douglas Bag) the total volume of gas expired in a minute is collected into a bag and its volume and composition of % of oxygen is measured afterwards. This is a very difficult and cumbersome method that requires particular technical skill and makes it impossible to evaluate the breath model.

Another method is based on a mixing chamber for the expired gas, wherein there is measured the expired volume and the average composition in a mixing chamber connected to the outflow of a two way respiratory valve. The rapid variations of oxygen concentration at mouth are smoothened and braked by the chamber volume allowing a steady measurement. This technique has been developed to allow the measure of oxygen consumption with gas analyzers with slow response time, i.e. on the order of few seconds. This is an obsolete technique, requiring bulky instrumentation that allows accurate measurements at steady state only.

The oxygen concentration trend at mouth changes rapidly, while at exit of the two-way valve the trend relates only to expiration phase, since during inspiration there is no air movement. Inside the mixing chamber the changes are averaged until an average value is reached corresponding to expiration $FeO_2$.

Since the volume of the chamber is constant, the time necessary reach a steady $FeO_2$ is:
shorter at higher ventilation levels
longer at lower ventilation levels This phenomenon, well known and described in literature, prevents the use of the mentioned technique whenever there is a rapid change of the ventilation in a minute; however the accuracy during steady state is anyway guaranteed.

Another technique is the so called "breath by breath" method. It consists of simultaneous real-time acquisition of inspired/expired flow and oxygen fraction at the mouth with the subsequent numerical integration of those signals. This method requires gas analyzers with a response time lower than 150 ms.

A further method, so-called "intelligent" proportional sampling technique of the expiration oxygen fraction, already described in patents U.S. Pat. No. 4,631,966 and U.S. Pat. No. 4,658,832. those patents describe a method with some drawbacks related to the analog characteristic of the devices to which they refer and to the little reliability of the pneumatic and electronic systems.

SUMMARY OF THE INVENTION

An objective of this invention is to provide a device for the measurement of oxygen consumption reliable for both low ventilation and high ventilation levels.

Further target is to develop a device for the measurement of oxygen consumption of simple and inexpensive make to allow the diffusion in different market areas.

The present invention, therefore, solves the above discussed drawbacks, according to a first aspect of the invention, by providing a device for the measurement of oxygen consumption incorporating a flowmeter (2) adapted to measure the exhaled gas flow of a person whose breathed flow is monitored, a mixing chamber (4), a duct (10) adapted to convey a portion of the exhaled air into the mixing chamber (4), detectors for detecting percentage of O2 of the exhaled gas within the mixing chamber (4), electronic control means (8) adapted to process parameters associated with the breathed flow, a constant flow rate aspirating pump (5) connected to the mixing chamber (4), a three-way valve (6) positioned between the constant flow rate aspirating pump (5) and the mixing chamber (4) adapted to open and close communication means (11) between said pump (5) and said mixing chamber (4).

According to another aspect of the invention, the above mentioned limitations are solved with a method for the measurement of oxygen consumption of a subject whose breathed flow is monitored, comprising the following stages: a) detecting and measuring an exhaled air of the subject by means of a flowmeter and transferring a relative measurement to a control means; b) supplying a portion of the exhaled air to a mixing chamber through communication means; c) activating a three-way valve to connect the mixing chamber with a constant flow rate aspirating pump during an exhalation by the subject, and to connect the pump to an outside environment when the exhalation stops; d) detecting a percentage of O2 inside the mixing chamber and communicating the percentage of O2 to the control means, and e) processing the detected percentage of O2 by the control means so as to calculate data on oxygen consumption of the subject.

The device described in this invention and the related method of measurement combines the advantages of all the measurement methods at the state of the art, such as:
- miniaturized mixing chamber that reduce the size of the entire device;
- accuracy and reliability of the measurements both at rest ($V_E$ very low) and during exercise ($V_E$ very high);
- simplicity of calibration procedures, particularly because calibration gas is not required;
- possibility to use a "slow response time" oxygen sensor, typically small and inexpensive.

The invention, furthermore, obtains the result to eliminate the drawbacks of the system using the classic "mixing chamber" technology, which are, for instance, higher dimensions of the mixing chamber, in the order of some liters; the need of a two way valve at the mouth and large diameter hose to convey the expired gas into the mixing chamber; a phase delay between the measured ventilation, which is instantaneous, and oxygen concentration fraction measurement, delayed with respect to the former by a time interval necessary to the mixing, variable with the ventilation per minute of the subject and following the impossibility to perform accurate measurements of oxygen consumption during protocols in which ventilation per minute changes rapidly.

Thanks to the use of a mixing microchamber, it is possible to obtain the same performance of a hypothetical device using a standard mixing chamber where hypothetically it would be possible to change the dimensions of the chamber in real time according to the ventilation per unit of time of the subject. This feature is obtained controlling dynamically the sampling rate, that is the quantity of expired gas conveyed inside the miniaturized mixing chamber, by means of a control system. The effect is a delay between ventilation measurement and expiration concentration which remains constant at any ventilation levels.

The dependent claims describe preferred embodiments of the invention.

BRIEF DESCRIPTION OF THE FIGURES

Further characteristics and advantages of the invention will become apparent in the light of a detailed description of a preferred embodiment, shown by way of non-limiting example with the aid of the enclosed drawings in which.

DETAILED DESCRIPTION OF A PREFERRED EMBODIMENT OF THE INVENTION

Figure 1:
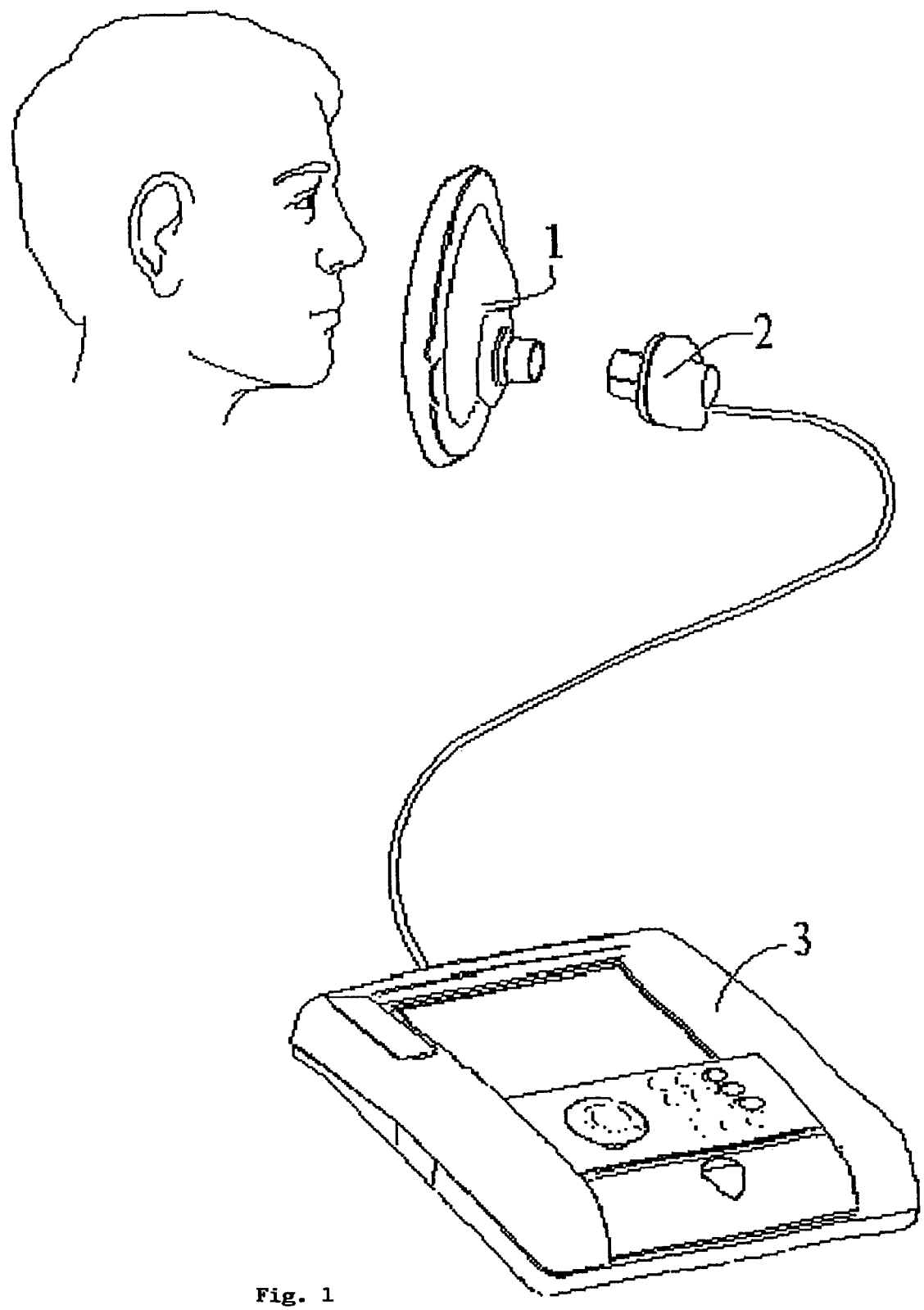
FIG. 1 shows an axonometric view of the device for measurement of oxygen consumption according to the present invention.

With reference to FIG. 1, there is shown a device for measurement of oxygen consumption device 3 for measurement of oxygen consumption, a face mask 1 and a flowmeter 2, for instance a turbine flowmeter.

Device 3 can operate powered by the internal batteries or connected to the mains and can be interfaced with a Personal Computer, a PDA (Personal Data Assistance) or similar.

Figure 2:
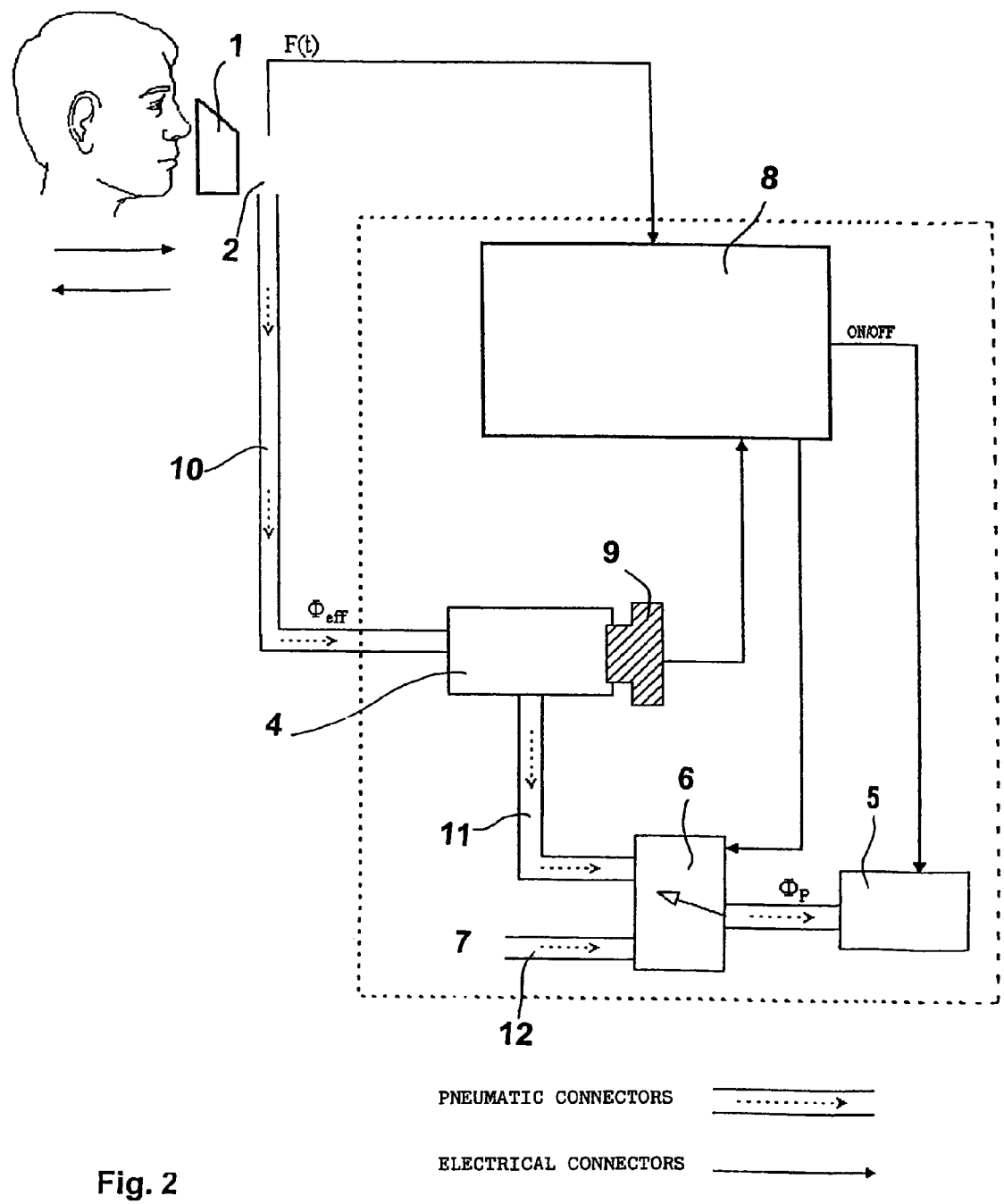
FIG. 2 shows the block diagram of the device for measurement of oxygen consumption according to the present invention.

The main functions of the system can be described referring to the block diagram of FIG. 2: Device 3 incorporates a miniaturized mixing chamber 4, and oxygen sensor 9, a sampling pump 5, a three-way valve 6 and control system 8. Miniaturized mixing chamber 4 has a size optimized according to the desired time necessary to mix the gas, that will be constant and according to the ventilation of subject.

The electropneumatic scheme of device 3 shown in FIG. 2 is described in more detail.

Device 3 furthermore incorporates advantageously a graphical display, a keyboard, an internal elaboration unit, a printer, and electrical and pneumatic connectors.

During the measurement a face mask 1 is applied to the subject. Face mask 1 is connected to the flowmeter 2, for instance a turbine flowmeter, that is the device in charge to measure the quantity of air inhaled and exhaled by the subject during the acquisition. Signals acquired by the Flowmeter 2 are transferred to the elaboration and control unit 8.

The control system 8 collects also the measurement of ventilation $V_E$ by processing the signals coming from Flowmeter 2 through appropriate sensors.

A significant portion of the air exhaled by the subject is transported through the sampling line 10, connected to the output of the flowmeter 2, into the miniaturized mixing chamber 4. This sampling line 10 has a very small internal diameter if compared with traditional mixing chamber devices, resulting therefore lighter and more comfortable. In inhalation phase the subject collects air from outside the mask 1 but not from sampling line 10 due to the design of the mask.

During measurement, sampling pump 5 has a constant flow rate $\Phi_p$. Pump 5 can be turned on or off by means of a switch which can be the same or different to the one of the device 3 itself. The three-way valve 6 is controlled with a pulsed waveform modulation (PWM) technique making the pump aspirate, proportionally to the amplitude of the commands pulses, from miniaturized mixing chamber 4 or from environment 7 respectively from lines 11 and 12.

Actuation of valve 6, which connects sampling pump 5 with environment 7 or alternatively with microchamber 4, is activated according to the signals transmitted by Flowmeter 2 to the control system 8. When flowmeter 2 detects an exhalation of the subject, transmits this data to the control system 8 that activates valve 6 to connect pump 5 to microchamber 4. In this way a significant portion of exhaled air is transferred inside the microchamber 4 while the subject is exhaling air through line 10 to microchamber 4. At the end of the exhalation phase, flowmeter 2 detects the interruption of the exhalation cycle and communicates this to the control system 8 that activates valve 6 to connect sampling pump 5 to line 12 allowing to sample air from environment 7.

The control system 8 receives information from oxygen sensor 9 also, to acquire percentage of Oxygen within mixing microchamber 4. Elaborating those signals the oxygen consumption is finally calculated.

The electro-pneumatic circuit shown in FIG. 2 is based on the following principles which allow the control system 8 to provide the final information on oxygen consumption and advantageously also on other data considered interesting.

Having defined K a proportional factor, the following relationship is desired:

$$K = \frac{V_{MSC}}{V_{MC}}$$

Where VMSC is the volume of a conventional mixing chamber, i.e. one that would be used in a device using the state of the art technology and $V_{MC}$ is the volume of a mixing microchamber 4 of device 3, where only a portion of the exhaled air is conveyed, that is 1/K.

To obtain a measurement of oxygen consumption equivalent to that of a traditional device, having a mixing chamber of greater dimensions, the proportion of volumes $V_{MCS}$ and $V_{MC}$ must correspond to a proportion between the sampling flow $\Phi_{\mathit{eff}}$, i.e. the quantity of exhaled air that passes inside the mixing microchamber 4, and of the total exhaled Flow F(t). To let flow in the mixing microchamber 4 a flow proportional to the total flow, i.e. $\Phi_{\mathit{eff}}$=F(t)/K a sampling pump 5, operating with a constant flow and a three-way valve 6 is used in the circuit.

Valve 6, set between mixing microchamber 4 and pump 5, is controlled with a pulsed waveform modulation (PWM) technique so as to aspirate alternatively either from mixing microchamber 4 or from environment 7 proportionally to pulse amplitude.

Pump 5 operates with a constant rate $\Phi_P$; defining T the period of the PWM command, %DC its duty cycle and $t_d$=%DC*T the time interval when the control signal is activated during a PWM period, the following volume is transferred inside the mixing microchamber 4:

$$V_T = \Phi_P * t_d = \Phi_P * \%DC * T$$

Being the period T of the command PWM the reference time, and reading the instantaneous value of the total flow F(t), %D must be updated in real time, taking into account that in the period T:

$$\Phi_{\mathit{eff}} = V_T/T$$

Therefore:

$$F(t) = K * \Phi_{\mathit{eff}} = K * \Phi_P * \%DC$$

Oxygen Consumption is calculated as follows using a system based on a mixing microchamber is given by the volume of inhaled oxygen less the exhalated one in relation to ventilations $V_E$, in l/min:

$$VO_2 = V_E \cdot \frac{(20.93 - FeO_2)}{100};$$

where $$V_E = 60 * \frac{1}{T} \int_0^T F(t) dt \text{ (l/min)}$$

The equations above need to be applied considering the response time of the system.

In the device 3 the value of $V_E$ is measured by the flowmeter 2 while the value of $FeO_2$ by the oxygen sensor 9. The measurement of $V_E$ is instantaneous but the corresponding value of $FeO_2$ sensed inside the mixing microchamber 4 is time delayed.

In accordance with the invention the value of the ventilation $V_E$ is associated to the appropriate oxygen percentage $FeO_2$ related to it, taking into account the total delay between the two values, given by the sum of two different delays: T1 and T2, wherein T1 is the time necessary to allow the sample air to pass through the sampling line 10 plus the response time of the oxygen sensor 9;

T2 is the time necessary to obtain an $O_2$ concentration inside the mixing microchamber 4 after having introduced a mix at the entrance of the chamber and:

$$T2 = \frac{X}{VE}$$

where X is the shape factor of the microchamber 4.

Therefore the total delay $T_d$ between ventilation $V_E$ and oxygen concentration $FeO_2$ is:

$$T_{V_E} \geq T_d = T1 + T2 = T1 + \frac{X}{V_E}$$

To keep constant the time delay between the measurements of $FeO_2$ and the ventilation on the whole measurement range envisaged, a dynamic update of the proportional factor K is necessary to maintain the total delay constant within the entire range of $V_E$ (from Rest to vigorous exercise).

Ignoring T1 and defining as $V_{E1}$ the total quantity of expired gas that would transit inside the mixing chamber of a conventional system, we obtain:

$$Td \approx \frac{X}{VE} = X \cdot \frac{K}{VE1}$$

The device according to this invention presents a constant mixing time T' as follows:

$$Td \approx X \cdot \frac{K}{VE1} = T'$$

Since the ventilation of the subject $V_{E1}$ varies and the volume V of the mixing mincrochamber 4 does not, in order to match the previous equation it is necessary to modify the proportional factor K according to the measured ventilation (rest-exercise).

The relationship between the shape index X of the microchamber 4 and its volume V is linear, i.e.

$$X = \mathrm{cost} \cdot V$$

therefore replacing the value of X in the equation of $T_d$ $$Td \approx \mathrm{cost} \cdot V \cdot \frac{K}{VE1} = T' \rightarrow K = \frac{T' \cdot VE1}{\mathrm{cost} \cdot V}$$

Assuming for instance the volume of the mixing microchamber 4 rather small, e.g. equal to V=100 ml and considering the typical values of $V_E$ from rest to exercise, it is possible to calculate the values of K to obtain a mixing time $T_d$.

For instance, with the person under test at rest, the following value is obtained:

$$VE1 = 6 \text{ l/min} \rightarrow Krest = \frac{T' \cdot 6}{\mathrm{cost} \cdot 100}$$

during vigorous exercise of the person under test $$VE1 = 200 \text{ l/min} \rightarrow Kexercise = \frac{T' \cdot 200}{\text{cost} \cdot 100}$$

Knowing the value of the proportion constant (cost) between the volume of the microchamber V and its shape factor X, one calculates the numeric values $K_{rest}$ and $K_{exercise}$ with reference to the two examples considered. The proportional factor K continuously changes according to the ventilation of the subject under test, according to the following equation:

$$K(VE) = \frac{T' \cdot VE1}{\text{cost} \cdot V}$$

The proposed solution for this invention has the effect to keep time delay $T_d$ constant increasing the accuracy of measurement and allowing compensation of time delay between ventilation $V_E$ measurement and that of $FeO_2$ which exists in the conventional mixing chamber systems. Furthermore the proposed solution has the advantage to reduce the size of the mixing chamber as desired, even to a reduction of 1/500 of the volume of known mixing chambers. Furthermore the time delay between $V_E$ and $FeO_2$ is kept constant by means of a dynamic update of the constant K, allowing a precise measurement of the oxygen consumption also under rapid ventilation changes.

Furthermore the oxygen consumption measurement device according to this invention is optimal to perform the following assessments:
- measurement of the resting metabolic rate of a person with the indirect calorimetry technique and calculation of the optimal daily caloric intake for the desired weight management program;
- measurement of the Maximal Oxygen uptake during an exercise test performed on a cycle ergometer or treadmill;
- measurement of energy expenditure during any physical activities in application such as weight management, fitness, sport medicine, preventive medicine, rehabilitation, etc . . .

The invention claimed is:

1. A device for measurement of oxygen consumption incorporating a flowmeter adapted to measure the exhaled gas flow of a person whose breathed flow is monitored, a mixing chamber, a duct adapted to convey a portion of the exhaled air into the mixing chamber, detectors for detecting percentage of $O_2$ in the exhaled gas within the mixing chamber, an electronic control system adapted to process parameters associated with the breathed flow, a constant flow rate aspirating pump connected to the mixing chamber, a three-way valve positioned between and outside of the constant flow rate aspirating pump and the mixing chamber and adapted to open communication passage between said pump and said mixing chamber and close another communication passage between the pump and an outside environment when the flowmeter detects an exhalation by the person, and adapted to open the another communication passage between the pump and an outside environment and close communication passage between said pump and said mixing chamber when the flowmeter detects an interruption in the exhalation by the person.

2. A device according to claim 1 wherein the mixing chamber has a volume lower than 100 ml.

3. A method for the measurement of oxygen consumption of a subject whose breathed flow is monitored, comprising:
- detecting and measuring an exhaled air of the subject with a flowmeter and transferring a relative measurement to a control system;
- supplying a portion of the exhaled air to a mixing chamber (4) through a communication passage;
- activating a three-way valve to connect the mixing chamber with a constant flow rate aspirating pump during an exhalation by the subject, and to connect the pump to an environment when the exhalation stops;
- detecting a percentage of O2 inside the mixing chamber and communicating the percentage of O2 to the control system, and
- processing the detected percentage of O2 by the control system so as to calculate data on oxygen consumption of the subject.

4. The method of claim 3, wherein the detecting of percentage of O2 is measured from the portion of the exhaled air entering the mixing chamber, calculated as a ratio between a total exhaled flow F(t) and a proportional factor K continuously changing to the following equation:

$$K(VE) = \frac{T \cdot VE}{\text{cost} \cdot V}$$

where VE is the subject's ventilation expressed in liters/second from a formula $$V_E = 60 * \frac{1}{T} \int_0^T F(t) dt,$$

where V is a volume of the microchamber, and where T is a constant mixing time.

5. A device for measurement of oxygen consumption comprising:
- a flowmeter that monitors and measures a breathed flow of exhaled air of a person; a mixing chamber;
- a duct that conveys a portion of the exhaled air into the mixing chamber; detectors for detecting percentage of O2 of the exhaled air within the mixing chamber; and
- electronic control system that measures the percentage of O2 from the portion of the exhaled air entering the mixing chamber, calculated as a ratio between total exhaled flow F(t) and a proportional factor K continuously changing to the following equation:

$$K(VE) = \frac{T \cdot VE}{\text{cost} \cdot V}$$

where VE is the person's ventilation expressed in liters/second from a formula $$V_E = 60 * \frac{1}{T} \int_0^T F(t) dt,$$

where V is a volume of the microchamber, and where T is a constant mixing time.

6. The device according to claim 5 wherein the mixing chamber has a volume lower than 100 ml.

* * * * *

UNITED STATES PATENT AND TRADEMARK OFFICE
CERTIFICATE OF CORRECTION

PATENT NO. : 7,621,271 B2 Page 1 of 1
APPLICATION NO. : 11/172305
DATED : November 24, 2009
INVENTOR(S) : Paolo Brugnoli It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1090 days.

Signed and Sealed this

Twenty-sixth Day of October, 2010

David J. Kappos
*Director of the United States Patent and Trademark Office*